(12) United States Patent
Okamoto

(10) Patent No.: US 11,607,113 B2
(45) Date of Patent: Mar. 21, 2023

(54) EXTERNAL MECHANISM FOR ENDOSCOPE AND ENDOSCOPE SYSTEM

(71) Applicant: OLYMPUS CORPORATION, Tokyo (JP)

(72) Inventor: Yasuhiro Okamoto, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 297 days.

(21) Appl. No.: 16/901,518

(22) Filed: Jun. 15, 2020

(65) Prior Publication Data

US 2020/0397227 A1 Dec. 24, 2020

Related U.S. Application Data

(63) Continuation of application No. PCT/JP2018/045840, filed on Dec. 13, 2018.

(30) Foreign Application Priority Data

Dec. 18, 2017 (JP) .............................. JP2017-241494

(51) Int. Cl.
*A61B 1/00* (2006.01)
*A61B 1/005* (2006.01)

(52) U.S. Cl.
CPC ........ *A61B 1/00055* (2013.01); *A61B 1/0052* (2013.01); *A61B 1/00105* (2013.01); *A61B 1/00042* (2022.02)

(58) Field of Classification Search
CPC .............. A61B 1/0052; A61B 1/00105; A61B 1/00066; A61B 1/00131; A61B 1/00137; A61B 1/0014; A61B 1/00147; A61B 1/0051; A61B 1/0016

USPC ................................................ 600/146–147
See application file for complete search history.

(56) References Cited

U.S. PATENT DOCUMENTS

| | | |
|---|---|---|
| 2002/0103418 A1 | 8/2002 | Maeda et al. |
| 2007/0238927 A1 | 10/2007 | Ueno et al. |
| 2007/0255103 A1* | 11/2007 | Maruyama ........... A61B 1/0052 600/149 |

(Continued)

FOREIGN PATENT DOCUMENTS

| | | |
|---|---|---|
| EP | 1818005 A1 | 8/2007 |
| EP | 2596741 A1 | 5/2013 |

(Continued)

OTHER PUBLICATIONS

English Translation of Takahashi (JPH05300873A), foreign copy provided by the Applicant. English translation through Espacenet. (Year: 1993).*

(Continued)

*Primary Examiner* — Ryan N Henderson
*Assistant Examiner* — Pamela F Wu
(74) *Attorney, Agent, or Firm* — Scully, Scott, Murphy & Presser, P.C.

(57) ABSTRACT

An external mechanism for endoscope includes a bending wheel, a motor, a housing case, a case detachably fixing member, and a mounting restricting member obstructing mounting of a housing case on a sub operation section by interfering with a second bending upward and downward fixing lever in a state where the second bending upward and downward fixing lever is at a position other than a release position.

18 Claims, 12 Drawing Sheets

(56) References Cited

U.S. PATENT DOCUMENTS

2010/0268031 A1* 10/2010 Koyama .............. A61B 1/0051
                                                                        600/146
2013/0184528 A1    7/2013  Onuki et al.
2014/0296632 A1  10/2014  Onuki et al.

FOREIGN PATENT DOCUMENTS

| EP | 2957214 A2 | 12/2015 |
|---|---|---|
| JP | H05-300873 A | 11/1993 |
| JP | 2002-224016 A | 8/2002 |
| JP | 2008-048788 A | 3/2008 |
| WO | WO 2006/059721 A1 | 6/2006 |
| WO | WO 2012/063880 A1 | 5/2012 |
| WO | WO 2012/111761 A1 | 8/2012 |

OTHER PUBLICATIONS

International Search Report dated Mar. 26, 2019 issued in PCT/JP2018/045840.

* cited by examiner

EXTERNAL MECHANISM FOR ENDOSCOPE AND ENDOSCOPE SYSTEM

CROSS REFERENCE TO RELATED APPLICATION

This application is a continuation application of PCT/JP2018/045840 filed on Dec. 13, 2018 and claims benefit of Japanese Application No. 2017-241494 filed in Japan on Dec. 18, 2017, the entire contents of which are incorporated herein by this reference.

BACKGROUND OF THE INVENTION

1. Field of the Invention

The present invention relates to an external mechanism for endoscope which is detachably mounted on a bending operation knob of an endoscope and configured to bend a bending portion disposed on an insertion section by rotating the knob using a drive force of a motor unit, and an endoscope system.

2. Description of the Related Art

Endoscopes have been used in a medical field, an industrial field and the like. The endoscopes are provided with a bending portion at an elongated insertion section which is inserted into a subject.

Japanese Patent Application Laid-Open Publication No. 2008-48788 discloses an endoscope including a first bending portion and a second bending portion which are disposed on a distal end side of an elongated insertion section, and are arranged parallel to each other in an extending direction of the insertion section. A main bending operation device and a sub bending operation device are mounted on an operation section positioned on a distal end side of the insertion section.

In such an endoscope, a bending operation of the first bending portion is performed by rotatably operating an operation knob of a main bending operation device, and a bending operation of the second bending portion is performed by rotatably operating an operation knob of a sub bending operation device.

Accordingly, a user can smoothly insert the insertion section into a complicatedly bent lumen by bending the first bending portion or the second bending portion by rotatably operating the respective operation knobs independently from each other. Further, it is possible to easily direct an observation optical system incorporated in a distal end side of the insertion section in a desired direction.

In the operation section described in Japanese Patent Application Laid-Open Publication No. 2008-48788, the sub bending operation device is, with respect to the main bending operation device, disposed on a proximal end side of the operation section on a side opposite to the insertion section in a spaced-apart manner from the main bending operation device.

Accordingly, it is difficult for a user to smoothly switch a rotary operation of the main bending operation device and a rotary operation of the sub bending operation device with fingers of a hand which grasps the operation section. Further, a large load is applied to the fingers of the user when the user rotatably operates the operation knobs of the bending operation devices.

In view of the above, there has been proposed an external electrically-operated bending mechanism which can be mounted on or removed from the operation section, and rotates, for example, the sub bending operation device by a drive force of a drive source such as a motor in a state where the electrically-operated bending mechanism is mounted on the operation section.

An endoscope used in general is provided with a holding member which holds an operation knob at a desired rotary position thus holding a bending state of a bending portion.

SUMMARY OF THE INVENTION

According to an aspect of the present invention, there is provided an external mechanism for endoscope which includes: a bending wheel engaging with a bending operation knob of a bending operation device provided to an operation section of an endoscope; a drive source configured to generate a drive force for rotating the bending wheel; a housing case housing the bending wheel and the drive source; a case detachably fixing member for detachably mounting the housing case on the operation section; and a mounting restricting member configured to obstruct mounting of the housing case on the operation section by interfering with a knob operation holding member, the knob operation holding member being provided to the operation section of the endoscope and being displaceable between a holding position at which a rotary position of the bending operation knob is held and a release position at which holding of the bending operation knob is released, in a state where the knob operation holding member is disposed at a position other than the release position.

Further, according to another aspect of the present invention, there is provided an endoscope system which includes: an endoscope; and an external mechanism detachably mounted on an operation section of the endoscope, wherein the endoscope includes: a bending knob provided to the operation section and configured to bend a bending portion of an insertion section by being rotated; and a knob operation holding member provided to the operation section, the knob operation holding member being displaceable between a holding position at which a rotation position of an operation knob is held and a release position at which holding of the operation knob is released by being operated, and the external mechanism includes: a wheel engaging with the bending knob so as to rotate the bending knob; a drive source configured to generate a drive force for rotating the wheel; a housing case housing the wheel and the drive source; a case detachably fixing member for detachably mounting the housing case on the operation section; and a mounting restricting member configured to obstruct mounting of the housing case on the operation section by interfering with the knob operation holding member in a state where the knob operation holding member is disposed at a position other than the release position.

DETAILED DESCRIPTION OF THE PREFERRED EMBODIMENT

Figure 1:
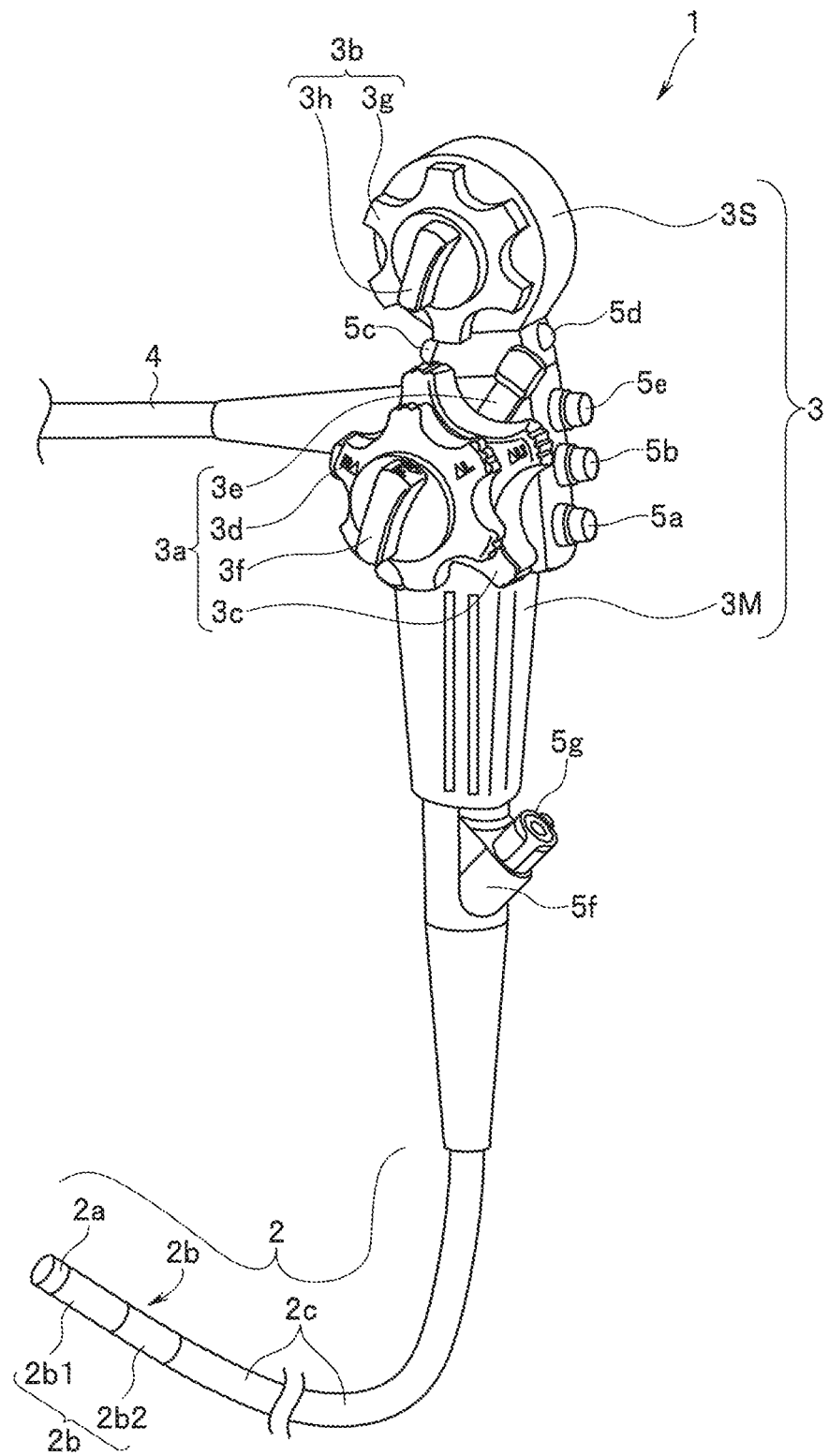
FIG. 1 is a view describing a configurational example of an endoscope.

An embodiment of the present invention is described with reference to drawings hereinafter.

In the respective drawings used in the description made hereinafter, to set sizes of respective constitutional components to a level that the respective constitutional components are recognizable on the drawings, scales are made different for the respective constitutional components. In other words, the present invention is not limited only to the number of constitutional components, shapes of the constitutional components, ratios between sizes of the respective constitutional components, and the relative positional relationships of the respective constitutional components shown in the drawings.

The configuration of an endoscope is described with reference to FIG. 1.

The endoscope 1 shown in FIG. 1 includes an elongated insertion section 2, an operation section 3 which also functions as a grasping portion and a universal cord 4. The insertion section 2 is formed by continuously connecting a distal end portion 2a, a bending portion 2b, and an elongated flexible tube portion 2c having flexibility in an order from a distal end side.

In the embodiment, the bending portion 2b has a first bending portion 2b1 and a second bending portion 2b2.

The first bending portion 2b1 is provided on a distal end side of the insertion section 2. The second bending portion 2b2 is continuously provided to a proximal end portion of the first bending portion 2b1 by way of a connecting portion (not shown).

The first bending portion 2b1 is bendable in upward, downward, leftward and rightward directions, for example. On the other hand, the second bending portion 2b2 is bendable in the upward and the downward directions.

The operation section 3 includes a first bending operation device 3a and a second bending operation device 3b.

In the embodiment, the operation section 3 includes: a main operation section 3M on which the first bending operation device 3a which also functions as a grasping portion is provided; and a sub operation section 3S which is provided on a proximal end side of the main operation section 3M and in which the second bending operation device 3b is provided.

The second bending operation device 3b is provided on an operation section proximal end side which is a side opposite to the insertion section 2 in a spaced-apart manner from the first bending operation device 3a.

The first bending operation device 3a includes: a first bending portion upward and downward operation knob (hereinafter abbreviated as a first bending upward and downward knob) 3c and a first bending portion leftward and rightward operation knob (hereinafter abbreviated as a first bending leftward and rightward knob) 3d which form bending operation knobs; and a first bending portion upward and downward direction fixing lever (hereinafter abbreviated as a first bending upward and downward fixing lever) 3e and a first bending portion leftward and rightward direction fixing tab (hereinafter abbreviated as a first bending leftward and rightward fixing tab) 3f which forms knob operation holding members.

The second bending operation device 3b includes: a second bending portion upward and downward operation knob (hereinafter abbreviated as a second bending upward and downward knob) 3g which forms a bending operation knob; and a second bending portion upward and downward direction fixing lever (hereinafter abbreviated as a second bending upward and downward fixing lever) 3h which forms a knob operation holding member.

The first bending upward and downward knob 3c is rotated at a time of bendably operating the first bending portion 2b1 in the upward and downward directions.

The first bending leftward and rightward knob 3d is rotated at a time of bendably operating the first bending portion 2b1 in the leftward and rightward directions. The first bending upward and downward fixing lever 3e is switchable between a holding position and a releasing position, and is displaced between the holding position and the releasing position.

The first bending leftward and rightward fixing tab 3f is switchable between a holding position and a releasing position, and is displaced between the holding position and the releasing position.

When the first bending upward and downward fixing lever 3e is at a free position, the first bending upward and downward knob 3c can be rotatably operated. At this time, the first bending portion 2b1 is brought into a state where the first bending portion 2b1 bends in the upward direction or in the downward direction along with a rotary operation of the first bending portion upward and downward knob 3c.

On the other hand, when the first bending leftward and rightward fixing lever 3f is at the releasing position, the first bending leftward and rightward knob 3d can be rotatably operated. At this time, the first bending portion 2b1 is brought into a state where the first bending portion 2b1 bends in the leftward direction or in the rightward direction along with a rotary operation of the first bending leftward and rightward knob 3d.

When the first bending upward and downward fixing lever 3e is switched to the holding position, the rotary position of the first bending upward and downward knob 3c is held.

As a result, a bending state of the first bending portion 2b1 in the upward and downward directions is held in a state at a time of switching the first bending upward and downward fixing lever 3e. In the same manner, when the first bending leftward and rightward fixing lever 3f is switched to the holding position, a rotary position of the first bending leftward and rightward knob 3d is held. As a result, the bending state of the first bending portion 2b1 in the leftward and rightward directions is held in a state at a time of switching the first bending leftward and rightward fixing tab 3f.

The second bending upward and downward knob 3g is rotated when the second bending portion 2b2 is bendably operated in the upward and downward directions. The second bending upward and downward fixing lever 3h is switchable between a holding position and a releasing position, and is displaced between the holding position and the releasing position.

When the second bending upward and downward fixing lever 3h is at the releasing position, the second bending upward and downward knob 3g can be rotatably operated. At this time, the second bending portion 2b2 is brought into a state where the second bending portion 2b2 bends in the upward direction or in the downward direction along with a rotary operation of the second bending upward and downward knob 3g.

When the second bending upward and downward fixing lever 3h is switched to the holding position, the rotary position of the second bending upward and downward knob 3g is held. As a result, a bending state of the second bending portion 2b2 in the upward and downward directions is held in a state at a time of switching the second bending upward and downward fixing lever 3h.

Reference numeral 5a indicates an air/water feeding button, reference numeral 5b indicates a suction operation button, reference numerals 5c, 5d, and 5e indicate remote switches, reference numeral 5f indicates a treatment instrument insertion opening, and reference numeral 5g indicates a forceps plug. The remote switches are switches for stopping an endoscope image displayed on a screen of a display device (not shown), recording of the image, enlargement of the image, switching of illumination light or the like. Optimum functions are allocated to the respective switches.

Figure 2A:
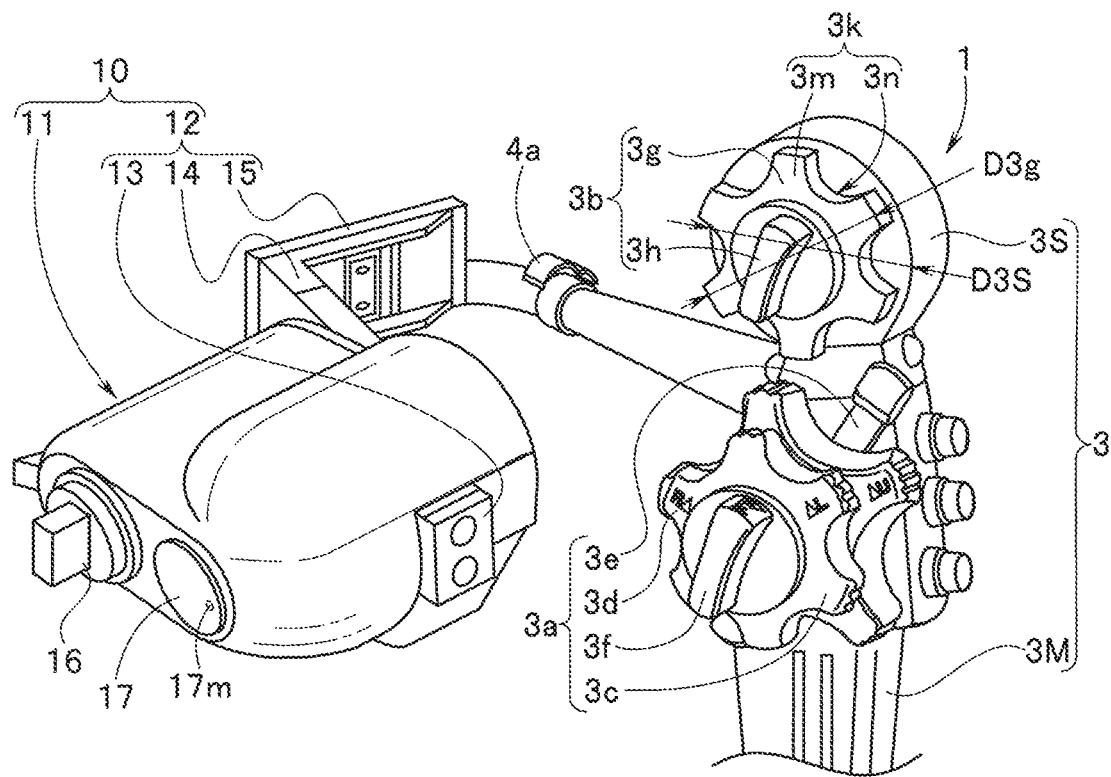
FIG. 2A is a view describing a relationship between a sub operation section which is an operation section of the endoscope and an external mechanism for endoscope.

In FIG. 2A, reference numeral 10 indicates an external mechanism for endoscope. The external mechanism for endoscope 10 is detachably mounted on the second bending upward and downward knob 3g provided on the sub operation section 3S.

The external mechanism for endoscope 10 is an auxiliary mechanism part which is mounted on the second bending upward and downward knob 3g and rotates the second bending upward and downward knob 3g by a drive force of a motor described later (see reference numeral 32 in FIG. 4B described later).

Reference numeral 11 indicates a housing case, and reference numeral 12 indicates a case detachably fixing member (hereinafter referred to as a case detachable portion). The case detachable portion 12 includes a locking portion 13, a hinge portion 14, and a locking pawl portion 15.

The locking portion 13 is fixedly provided on the housing case 11 at a preliminarily set position. The hinge portion 14 has an approximately L shape, and one end portion of the hinge portion 14 is rotatably placed in the housing case 11 at a preliminarily set position. The locking pawl portion 15 is provided on the other end portion of the hinge portion 14 having an L shape.

A rotary state of the hinge portion 14 is restricted by allowing the locking pawl portion 15 to engage with and to be fixed to the locking portion 13. Reference numeral 16 indicates a switching tab, and reference numeral 17 indicates a bending state display portion. The bending state display portion 17 has a rotation index 17m.

Figure 2B:
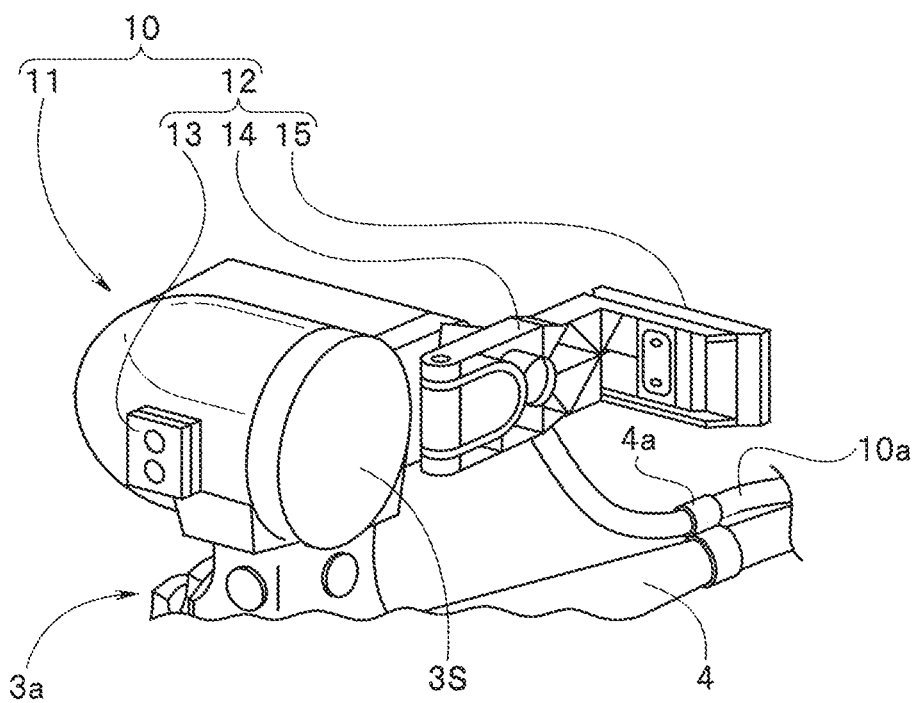
FIG. 2B is a view describing a state where the external mechanism for endoscope is disposed on the still operation section.

Reference numeral 4a indicates a cable mounting jig. As shown in FIG. 2B, one or a plurality of cable mounting jigs 4a are provided to the universal cord 4 at a desired position. An electric cable 10e is mounted on the universal cord 4 by the cable mounting jig 4a.

Figure 2C:
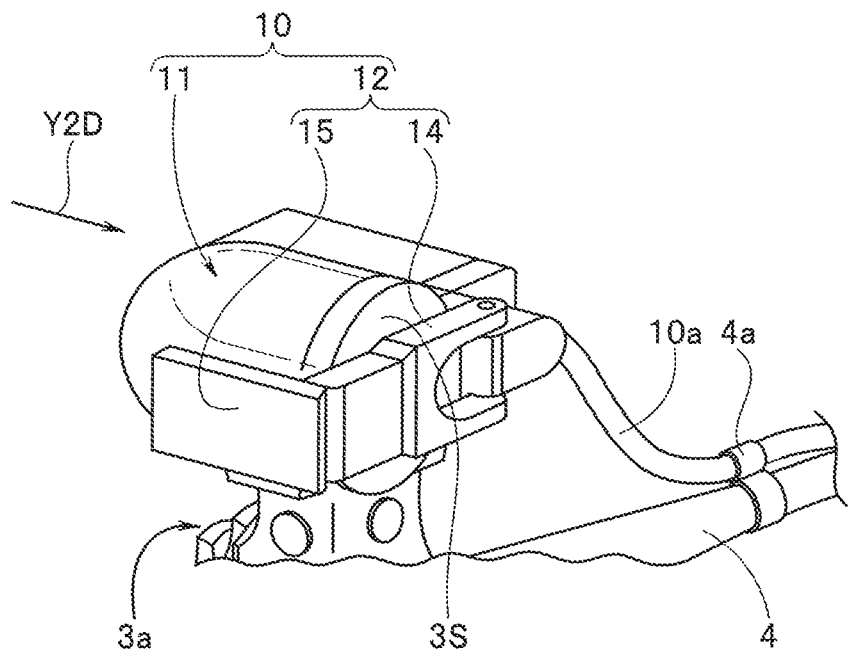
FIG. 2C is a view showing a state where the external mechanism for endoscope is mounted on and fixed to the sub operation section.
Figure 2D:
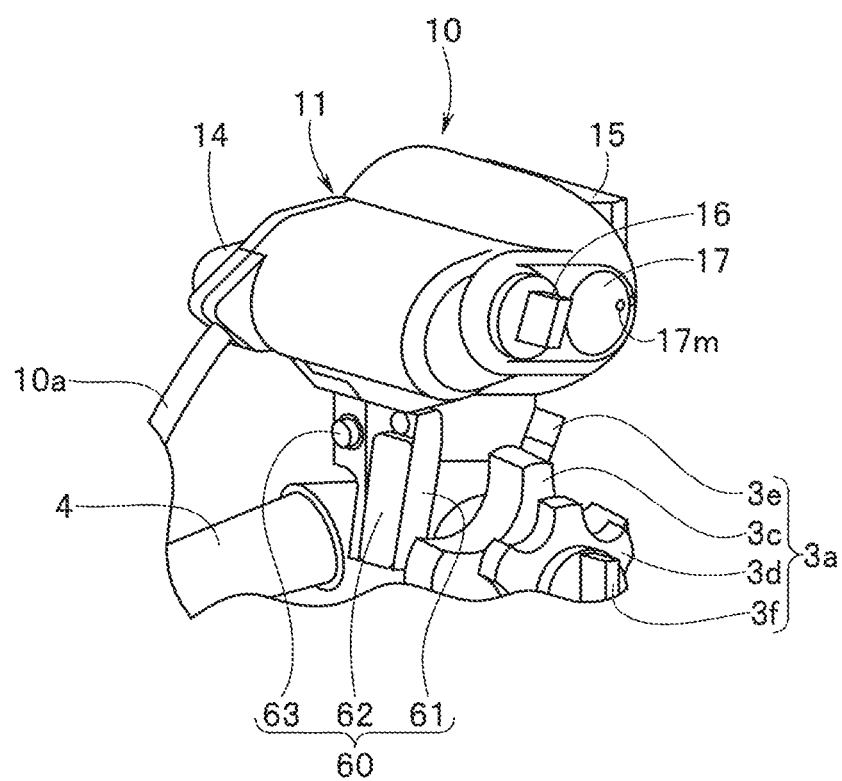
FIG. 2D is a view of the sub operation section in FIG. 2C as viewed from a side indicated by an arrow 2D.

As shown in FIG. 2B, the external mechanism for endoscope 10 is integrally mounted on the sub operation section 3S by causing the locking pawl portion 15 to engage with and to be fixed to the locking portion 13 by rotating the housing case 11 using one end portion side of the hinge portion 14 as a fulcrum as shown in FIG. 2C and FIG. 2D in a state where the housing case 11 is placed on the sub operation section 3S while covering the second bending upward and downward knob 3g.

In FIG. 2D, reference numeral 60 indicates an operation switch, reference numeral 61 indicates a switch case, reference numeral 62 indicates an operation element, and reference numeral 63 indicates a dummy switch.

The configuration of the external mechanism for endoscope 10 is described.

Figure 3:
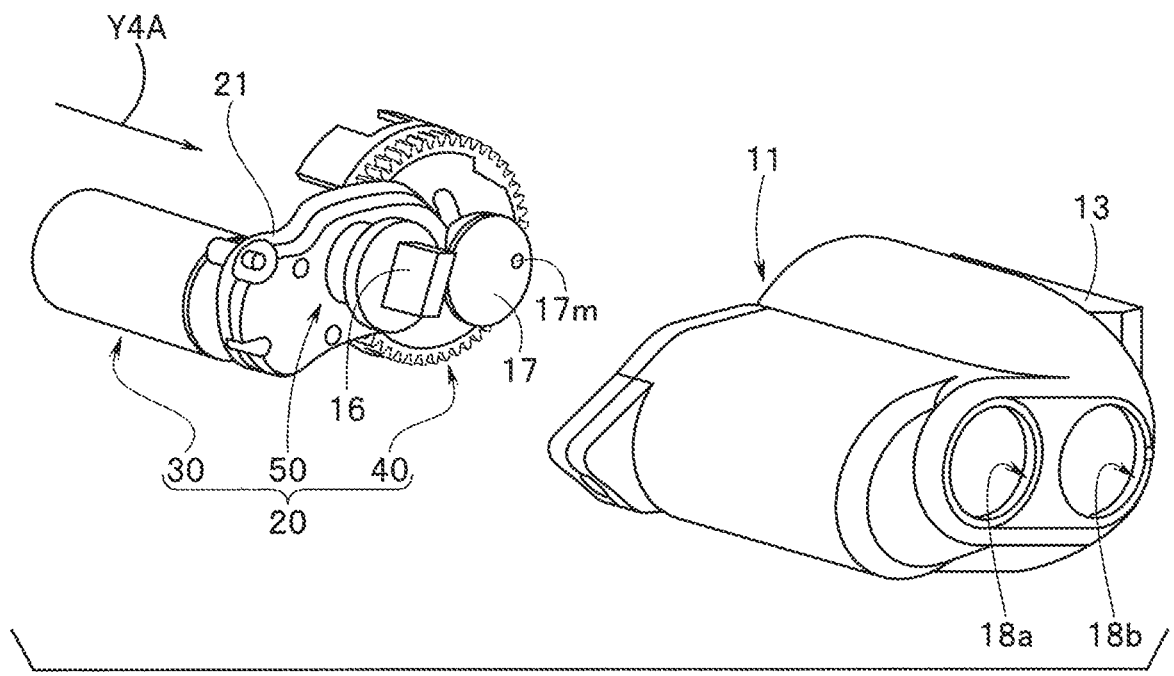
FIG. 3 is a view describing a relationship between a housing case of the external mechanism for endoscope and a knob rotating mechanism housed in the housing case.

As shown in FIG. 3, the housing case 11 of the external mechanism for endoscope 10 has a case inner space, and a knob rotating mechanism 20 is housed in the case inner space.

In the housing case 11, a first through hole 18a in which the switching tab 16 is placed, and a second through hole 18b in which the bending state display portion 17 is placed are provided. The case inner space and the outside communicate with each other through the through holes 18a, 18b.

The knob rotating mechanism 20 is described with reference to FIG. 3, FIG. 4A, and FIG. 4B.

As shown in FIG. 3, the knob rotating mechanism 20 mainly includes a motor portion 30, a knob rotating portion 40, and a transmission portion 50. In FIG. 3 to FIG. 4B, reference numeral 21 indicates a rotating mechanism portion body, and is also a mounting member.

Figure 4A:
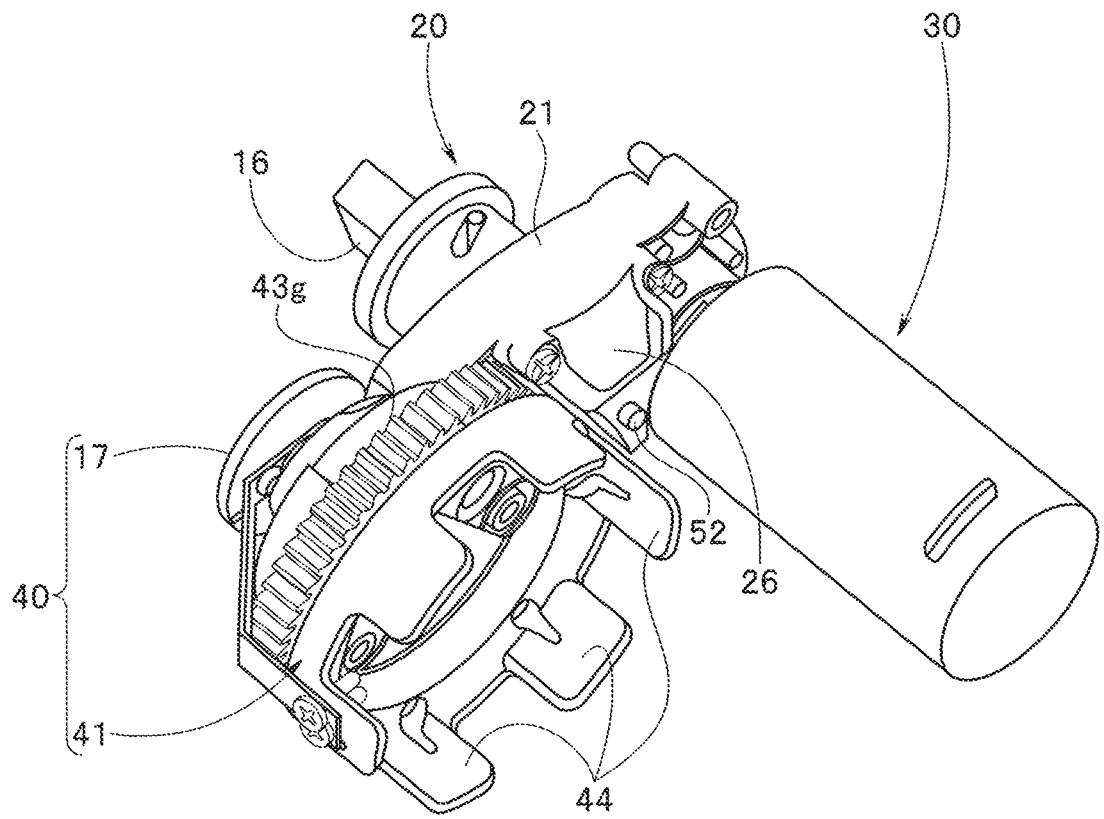
FIG. 4A is a view of the knob rotating mechanism as viewed from a direction indicated by arrow Y4A in FIG. 3.
Figure 4B:
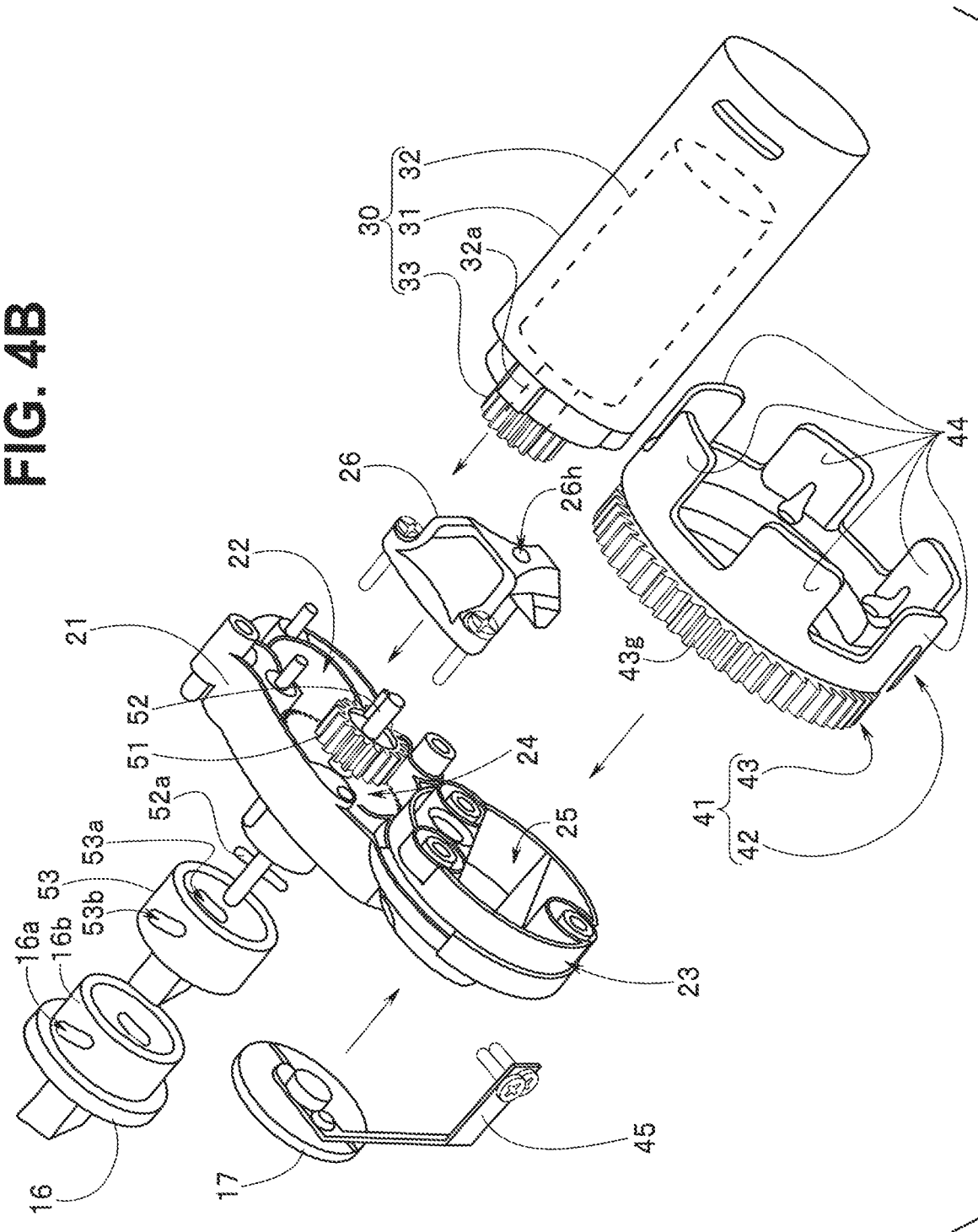
FIG. 4B is an exploded perspective view schematically describing the configuration of the knob rotating mechanism.

As shown in FIG. 4B a motor mounting portion 22, a wheel mounting portion 23, a switching gear mounting portion 24 and the like are provided on the rotating mechanism portion body 21 at preliminarily set positions.

Reference numeral 25 indicates an operation restricting portion which is provided on the mounting portion 23. The operation restricting portion 25 is a concave portion for lever, and is a recessed portion or a hole formed in a profile and a depth which allow the second bending upward and downward fixing lever 3h to be fitted into the operation restricting portion 25.

Reference numeral 26 indicates a switching gear support member. The switching gear support member 26 has a through hole 26h in which one end portion of a switching gear shaft 52 on which a switching gear 51 is fixedly provided is placed.

The switching gear support member 26 is fixedly provided on the rotating mechanism portion body 21 at a preliminarily set position, and rotatably and pivotally supports one end portion of the switching gear shaft 52 which is placed in the through hole 26h.

The motor portion 30 mainly includes: a motor case 31, a motor 32 indicated by a broken line which is a drive source; and a drive gear 33.

The motor 32 is placed in the motor case 31. The drive gear 33 is fixedly provided on a motor shaft 32a which protrudes from the motor 32.

As shown in FIG. 4A, the motor case 31 is fixedly provided on the motor mounting portion 22 in a preliminarily set state.

As shown in FIG. 4A and FIG. 4B, the knob rotating portion 40 includes a bending wheel 41 and the bending state display portion 17.

The bending wheel 41 includes a knob connecting portion 42 and a meshing portion 43 which are ring-shaped members. The knob connecting portion 42 and the meshing portion 43 are integrally fixed to each other.

The meshing portion 43 is a gear portion on an outer peripheral surface of which a gear 43g is formed. A plurality of convex portions 44 are arranged on the knob connecting portion 42 in a circumferential direction.

The plurality of convex portions 44 are respectively accommodated in concave portions 3n each of which is positioned between each two of a plurality of convex portions 3m of a concavo-convex portion (indicated by reference numeral 3k in FIG. 2A) which the second bending upward and downward knob 3g has.

By allowing the convex portions 44 to be placed in the concave portions 3m respectively, the second bending upward and downward knob 3g and the bending wheel 41 are integrally connected to each other. In an integrally connected state, the second bending upward and downward knob 3g is rotated together with the rotation of the bending wheel 41 in the rotating direction of the bending wheel 41.

The bending state display portion 17 is formed of a circular disc, and the rotation index 17m is provided on a front surface of the circular disc at a preliminarily set position. Reference numeral 45 indicates a connecting member, and one end portion of the connecting member 45 is integrally and fixedly provided on a back surface of the circular disc which forms the bending state display portion 17.

The other end portion of the connecting member 45 is integrally and fixedly provided on an outer peripheral surface of the knob connecting portion 42 of the bending wheel 41 at a preliminarily set position.

Accordingly, the bending state display portion 17 is rotated in the same direction together with the rotation of the bending wheel 41 in a clockwise manner or in a counter-clockwise manner. Accordingly, a user can easily determine a bending angle (bending amount) of the second bending portion 2b2 by checking the position of the rotation index 17m.

Figure 4C:
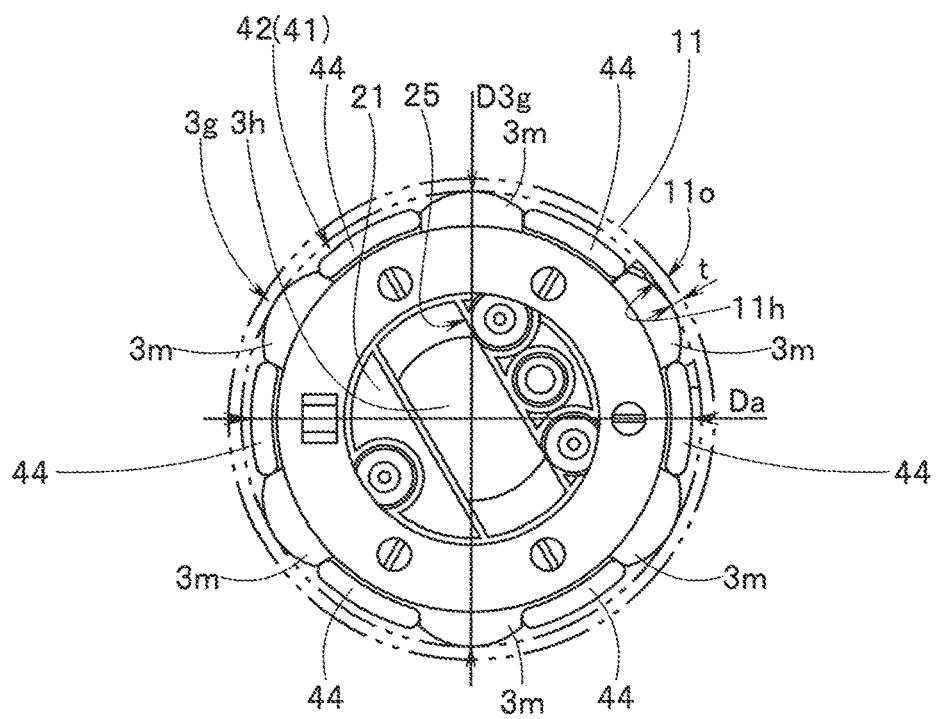
FIG. 4C is a view describing a mounting state where a convex portion of a knob connecting portion is placed in a concave portion of a second bending upward and downward knob in a predetermined state.

In the embodiment, as shown in FIG. 4C, an outer diameter Da of the knob connecting portion 42 of the bending wheel 41 is set smaller than an outer diameter D3g of the second bending upward and downward knob 3g. As shown in FIG. 2A, the outer diameter D3g of the second bending upward and downward knob 3g is preliminarily set smaller than an outer peripheral surface (described as an outer peripheral outer diameter D3S) of the sub operation section 3S such that the second bending upward and downward knob 3g is disposed inside the outer peripheral outer diameter D3S.

Accordingly, in a state where the bending wheel 41 is integrated with the second bending upward and downward knob 3g, the outer peripheral surface of the bending wheel 41 is positioned on a more center side than the outer peripheral surface of the second bending upward and downward knob 3g.

Reference numeral 11h indicates an inner peripheral surface of a knob rotating portion housing hole portion of the housing case 11. An inner diameter of the inner peripheral surface 11h is preliminarily set larger than the outer diameter D3g of the second bending upward and downward knob 3g.

Further, a wall thickness t of the housing case 11 is set such that an outer peripheral surface 11o of the knob rotating portion housing hole portion 11h and the outer peripheral surface of the sub operation section 3S become coplanar in a placement state.

The outer peripheral surface 11o of the knob rotating portion housing hole portion 11h may be set slightly larger than the outer peripheral surface of the sub operation section 3S.

In such a manner, the outer peripheral surface of the bending wheel 41 is set to be disposed on a more center side than the outer peripheral surface of the second bending upward and downward knob 3g.

A diameter of the outer peripheral surface 11o of the knob rotating portion housing hole portion 11h is set substantially equal to or slightly larger than a diameter of the outer peripheral surface of the sub operation section 3S by suitably setting the wall thickness of the knob rotating portion housing hole portion 11h of the housing case 11.

As a result, it is possible to prevent the occurrence of a state where, in a state where the profile shape of the housing case 11 is set small and the housing case 11 is placed on the sub operation section 3S so as to cover the second bending upward and downward knob 3g, the outer peripheral surface 11o of the knob rotating portion housing hole portion 11h of the housing case 11 largely protrudes from the outer peripheral surface of the sub operation section 3S and adversely affects the operation of the first bending upward and downward knob 3c, the operation of the first bending leftward and rightward knob 3d, the operation of the first bending upward and downward fixing lever 3e, or the like.

The transmission portion 50 is mainly includes the switching gear 51, the switching gear shaft 52, a cam ring 53, and the switching tab 16 shown in FIG. 4B.

Figure 4D:
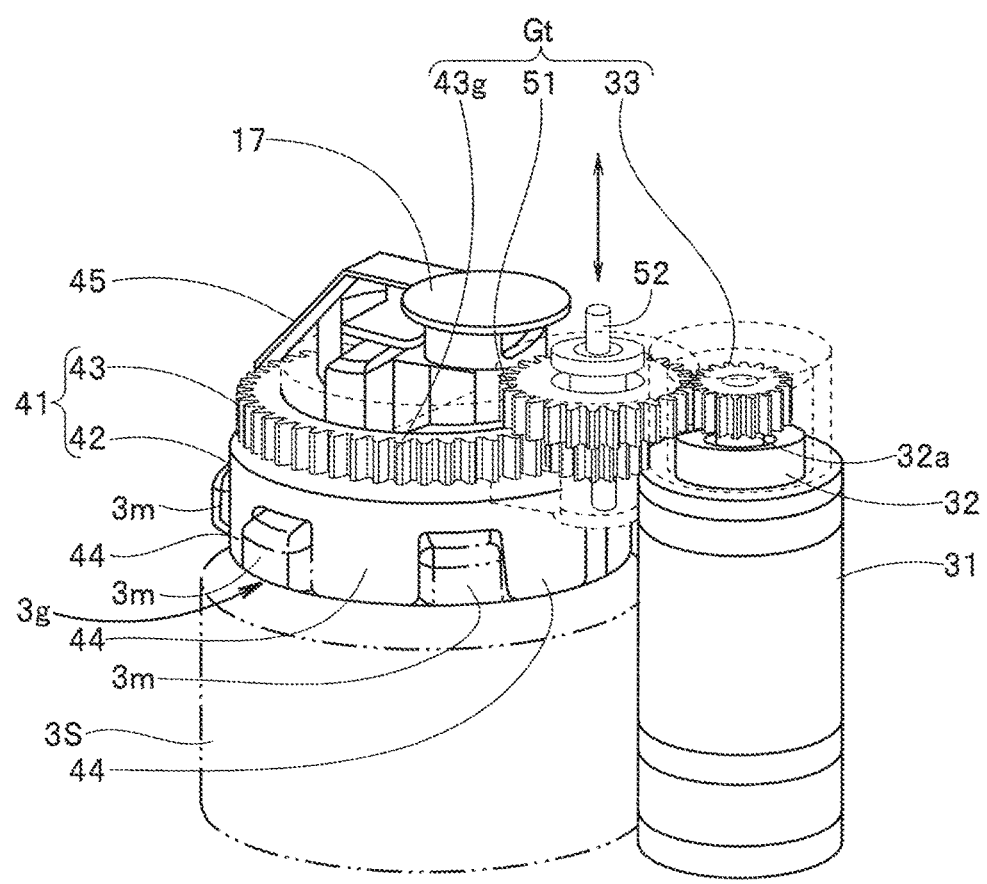
FIG. 4D is a view describing a gear train formed of a switching gear, a gear of a meshing portion, and a drive gear fixedly mounted on a motor shaft.

As described previously, the switching gear 51 is fixedly provided on one end portion side of the switching gear shaft 52. The switching gear 51 forms a gear train Gt as shown in FIG. 4D together with the gear 43g of the meshing portion 43 of the bending wheel 41 and the drive gear 33 fixedly provided on the motor shaft 32a which are described previously.

As shown in FIG. 4B, an engaging protrusion 52a which protrudes in a direction orthogonal to the switching gear shaft 52 is formed on the other end portion of the switching gear shaft 52.

A cam groove 53a for ring is formed on the cam ring 53. A protrusion 53b for ring protrudes from an outer peripheral surface of the cam ring 53. The switching tab 16 has a cylinder portion 16a, and a cam groove 16b for cylinder is formed on the cylinder portion 16a.

An outer peripheral surface side of the cam ring 53 is placed on an inner peripheral surface side of the cylinder portion 16a of the switching tab 16. In such a placement state, the protrusion 53b for ring is disposed in the cam groove 16b for cylinder.

On the other hand, the engaging protrusion 52a is placed on an inner peripheral surface side of the earn ring 53. In such a placement state, the engaging protrusion 52a is disposed in the cam groove 53a for ring.

With such a configuration, the protrusion 53b for ring disposed in the cam groove 16b for cylinder is moved together with the rotation of the switching tab 16 and hence, the cam ring 53 is moved in an axial direction of the switching gear shaft 52. Further, the engaging protrusion 52a in the cam groove 53a for ring is moved in the axial direction together with the movement of the cam ring 53 in the axial direction.

As a result of the operations, as shown in FIG. 4D, the switching gear 51 of the gear train Gt is moved with respect to the axial direction of the switching gear shaft 52 together with a switching operation of the switching tab 16 in a clockwise manner or in a counterclockwise manner and hence, an operation state is switched between a state where the switching gear 51 meshes with a gear 43c of the meshing portion 43 and the drive gear 33 and a state where the switching gear 51 is disconnected from the gear 43c of the meshing portion 43a and from the drive gear 33.

In the transmission state where the switching gear 51 meshes with the gear 43c of the meshing portion 43 and the drive gear 33, a rotation drive force of the motor 32 is transmitted to the bending wheel 41 and hence, the second bending upward and downward knob 3g is rotated.

In other words, by bringing the switching gear 51 and the gear 43c of the meshing portion 43 and the drive gear 33 into a disconnected state, there is no possibility that a drive three of the motor 32 is transmitted to the bending wheel 41.

Figure 4E:
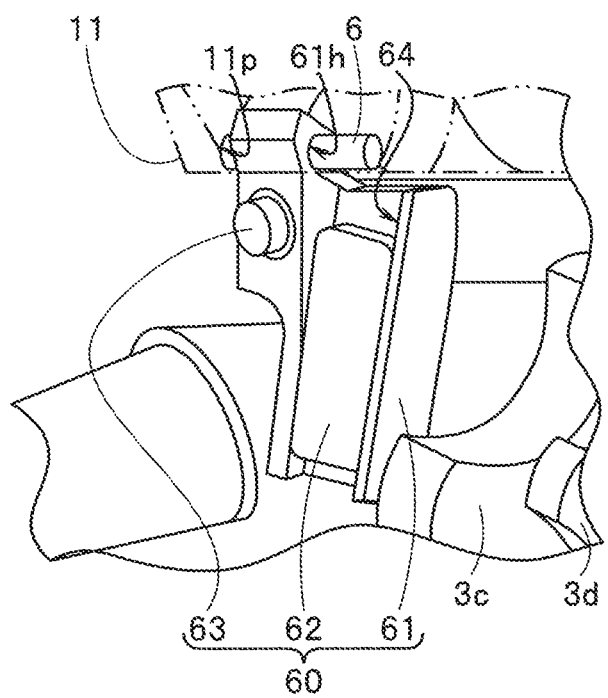
FIG. 4E is a view describing mounting of an operation switch on the housing case.

As shown in FIG. 4E, the operation switch 60 mainly includes the switch case 61, the operation element 62, and the dummy switch 63. The manner of operation of the dummy switch 63 is described later.

An operation element housing portion 64 and a pin hole 61h for hinge are provided in the switch case 61. Reference numeral 6 indicates a pin for hinge.

The pin 6 for hinge is disposed in a hole 11p for hinge provided in the housing case 11 and in the pin hole 61h for hinge. As a result, the switch case 61 is disposed rotatably with respect to the housing case 11 about the pin 6 for hinge.

Figure 5A:
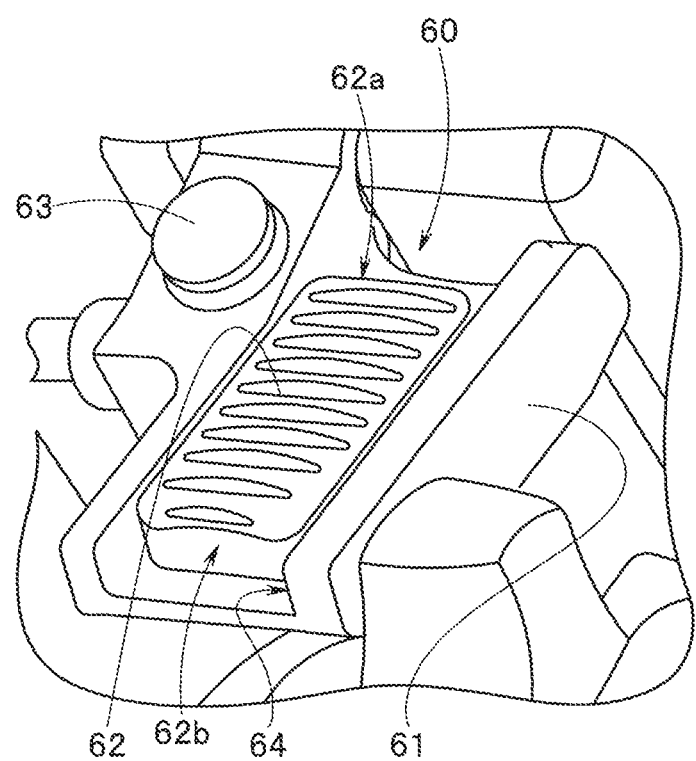
FIG. 5A is a view describing the configuration of the operation switch.

As shown in FIG. 5A, the operation element housing portion 64 is an elongated groove, and the operation element 62 is disposed in the operation element housing portion 64 slidably in the longitudinal direction. Accordingly, in the configuration shown in the drawing, the operation element 62 functions as a so-called slide switch.

Figure 5B:
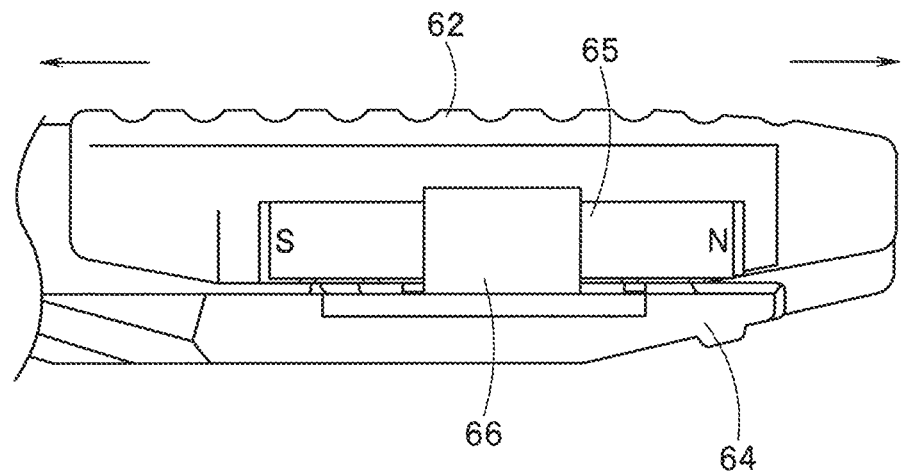
FIG. 5B is a view describing a configurational example where an operation element is a slide switch.

As shown in FIG. 5B, a magnet 65 is placed on the operation element 62 at a preliminarily set position, and a hall sensor (hereinafter abbreviated as a sensor) 66 which detects a magnetic field of the magnet 65 is provided on the case housing portion 64 at a preliminarily set position. The sensor 66 outputs a predetermined drive control signal to the motor in response to a change in distances from the sensor to an N pole and an S pole of the magnet 65.

More specifically, when a lower end 62b of the operation element 62 shown in FIG. 5A is positioned at a lowermost portion within a slide range of the operation element housing portion 64, the sensor 66 outputs a first drive control signal to the motor 32.

As a result, the motor 32 is rotatably driven at a high speed, for example, and rotates the second bending upward and downward knob 3g in a counterclockwise direction. Reversely, when an upper end 62a of the operation element 62 is positioned at an uppermost portion within the slide range, the sensor 66 outputs a third drive control signal to the motor 32.

As a result, the motor 32 is rotatably driven at a high speed, for example, and rotates the second bending upward and downward knob 3g in a clockwise direction.

When the upper end 62a of the operation element 62 is spaced apart from an intermediate portion between the uppermost portion and the lowermost portion to an upper portion side by a preliminarily set distance, the sensor 66 outputs a fourth drive control signal to the motor 32. As a result, the motor 32 is rotatably driven at a low speed, for example, and rotates the second bending upward and downward knob 3g in a clockwise direction.

Reversely, when the lower end 62b of the operation element 62 is spaced apart from the intermediate portion to a lower portion side by a preliminarily set distance, the sensor 66 outputs a second drive control signal to the motor 32. As a result, the motor 32 is rotatably driven at a low speed, for example, and rotates the second bending upward and downward knob 3g in a counterclockwise direction.

Figure 5C:
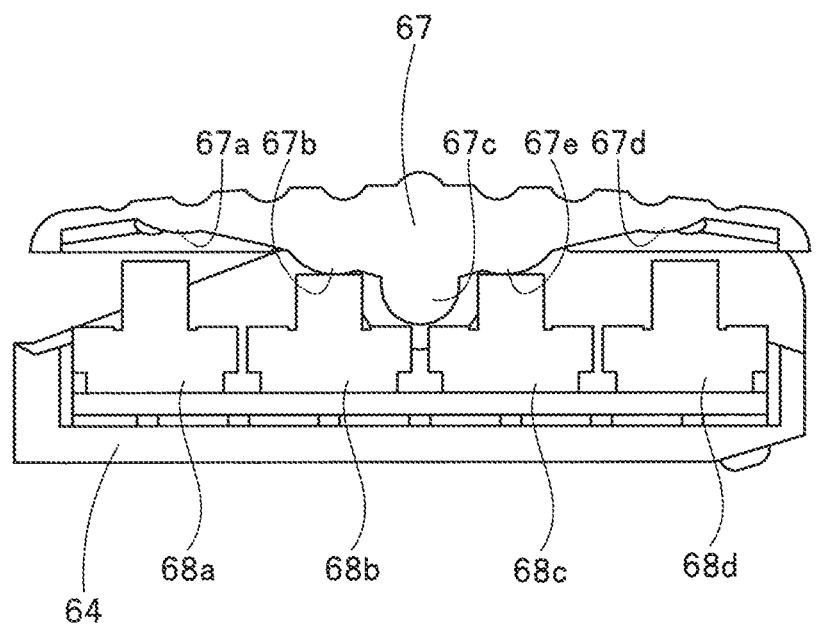
FIG. 5C is a view describing a configurational example where the operation element is a seesaw switch.

In the above-mentioned embodiment, the operation element 62 is formed of a slide switch. However, the operation element may be, as shown in FIG. 5C, a seesaw switch 67 which rotates in a clockwise manner or in a counterclockwise manner using, a center convex portion 67c as a fulcrum.

The seesaw switch 67 is provided with four switch convex portions 67a, 67b, 67d, and 67e. A plurality of, for example, four tactile switches 68a, 68b, 68c, and 68d are provided in the case housing portion 64.

When the seesaw switch 67 is in an initial state, the second tactile switch 68b and the third tactile switch 68c are in an ON state, and the first tactile switch 68a and the fourth tactile switch 68d are in an OFF state. At this time, the motor 32 is in a stopped state.

Figure 5D:
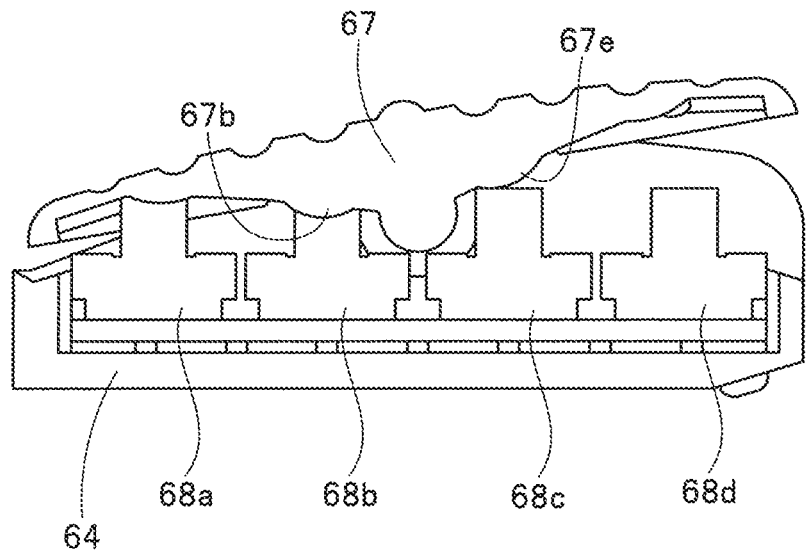
FIG. 5D is a view describing an operation example of the seesaw switch.

When the seesaw switch 67 is rotated in a counterclockwise manner so that, as shown in FIG. 5D, the third tactile switch 68c is switched from an ON state to an OFF state and only the second tactile switch 68b is in an ON state, a second drive control signal is outputted to the motor 32. As a result, the motor 32 is driven at a low speed and rotates the second bending upward and downward knob 3g in a counterclockwise direction.

Figure 5E:
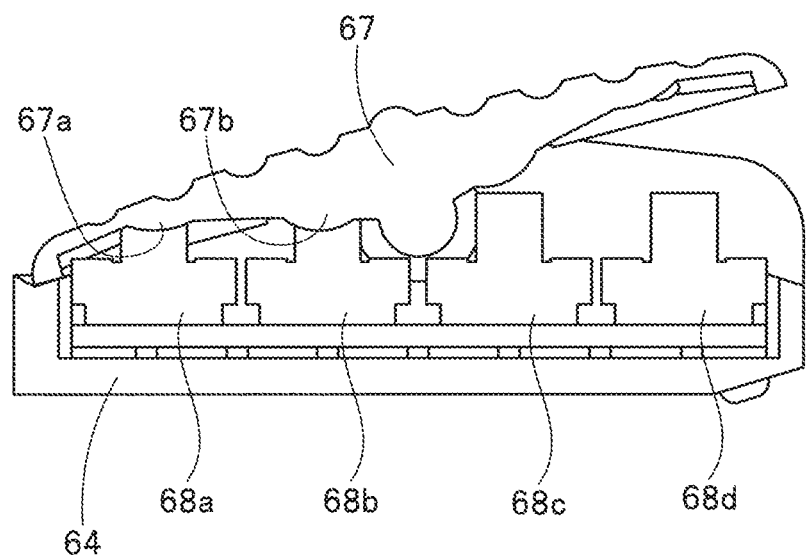
FIG. 5E is a view describing another operation example of the seesaw switch.

As shown in FIG. 5E, when the seesaw switch 67 is further rotated in a counterclockwise manner, the first tactile switch 68a is brought into an ON state in addition to the second tactile switch 68b. Accordingly, a first drive control signal is outputted to the motor 32. As a result, the motor 32 is driven at a high speed, and rotates the second bending upward and downward knob 3g in a counterclockwise direction.

Although not shown in the drawings, with the motor 32 held in a stopped state, when the seesaw switch 67 is rotated in a clockwise manner, the second tactile switch 68b is switched from an ON state to an OFF state and hence, only the third tactile switch 68c is brought into an ON state, and a fourth drive control signal is outputted to the motor 32. As a result, the motor 32 is driven at a low speed, and rotates the second bending upward and downward knob 3g in a clockwise direction.

Then, when the seesaw switch 67 is further rotated in a clockwise manner, the fourth tactile switch 68d is brought into an ON state in addition to the third tactile switch 68c. Accordingly, a third drive control signal is outputted to the motor 32. As a result, the motor 32 is driven at a high speed and rotates the second bending upward and downward knob 3g in a clockwise direction.

In this manner, due to a slide operation or a rotary operation of the operation element 62 provided to the operation element 60, a drive control signal is outputted to the motor 32, and a rotation control of the second bending upward and downward knob 3g is performed using a drive force of the motor 32.

As a result, a user can perform a bending operation of the second bending portion 2b2 without applying a large load to fingers.

In the above-mentioned embodiment, a speed is set at two stages including a high speed and a low speed. However, a drive control of the motor 32 may be performed so as to change a speed at one stage or three or more stages or in a stepwise manner based on a detection result of the hall sensor 66.

The speed may be changed in one stage or three or more stages by increasing or decreasing the number of the tactile switches and the number a the switch convex portions.

Mounting of the external mechanism for endoscope 10 on the sub operation section 3S is described with reference to FIG. 6 to FIG. 7D.

First, in mounting the housing case 11 of the external mechanism for endoscope 10 on the sub operation section 3S, a user preliminarily checks whether or not the second bending upward and downward fixing lever 3h which is provided on the second bending upward and downward knob 3b is at the release position.

Figure 6:
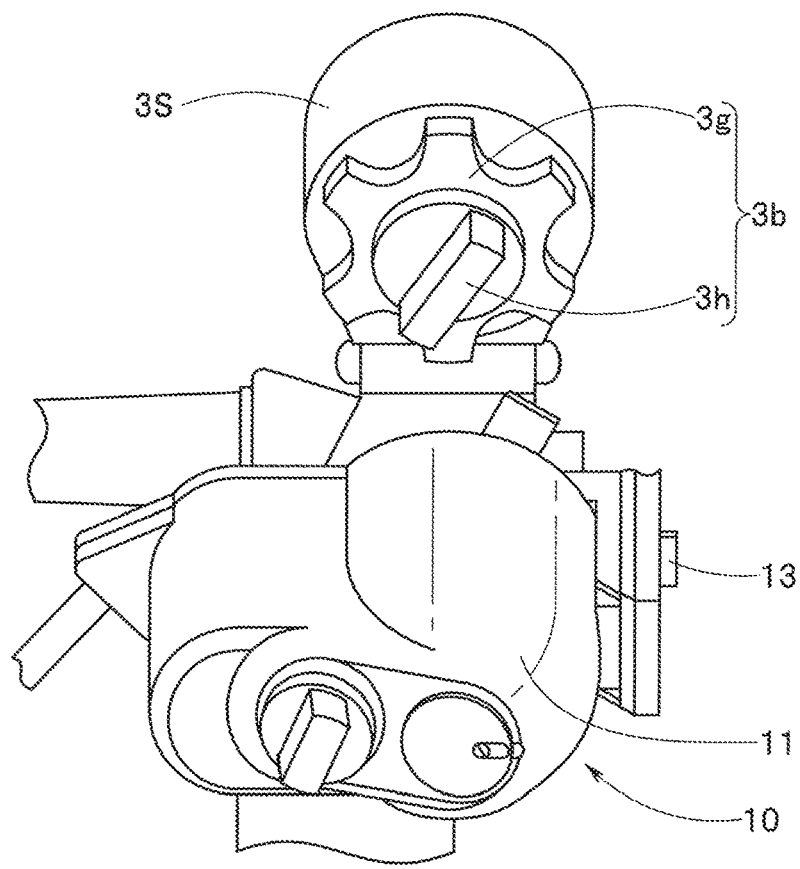
FIG. 6 is a view describing a state where the housing case of the external mechanism for endoscope is mounted on the sub operation section.

The user checks that the second bending upward and downward fixing lever 3h is disposed at the release position and, thereafter, allows the housing case 11 of the external mechanism for endoscope 10 to face the second bending upward and downward knob 3g provided on the sub operation section 3S as shown in FIG. 6.

At this time, the user allows the bending wheel 41 of the knob rotating portion 40 placed in the case inner space to face the second bending upward and downward knob 3g.

Next, the user allows the housing case 11 to approach the second bending upward and downward knob 3g. Then, the user allows the concave portion 25 for lever which is provided on the rotating mechanism portion body 21 and is positioned inside the inner periphery of the bending wheel 41 to face the second bending upward and downward fixing lever 3h, and allows the second bending upward and downward fixing lever 3h to be housed in the concave portion 25 for lever as shown in previously mentioned FIG. 4C. As a result, as shown in FIG. 2B, the housing case 11 is disposed on the second bending upward and downward knob 3g.

Further, in such a housing and placement state, as shown in previously mentioned FIG. 4C, the convex portions 44 of the knob connecting portion 42 are placed in the concave portions of the second bending upward and downward knob 3g in a predetermined state and hence, the second bending upward and downward knob 3g and the bending wheel 41 are integrated with each other.

Figure 7A:
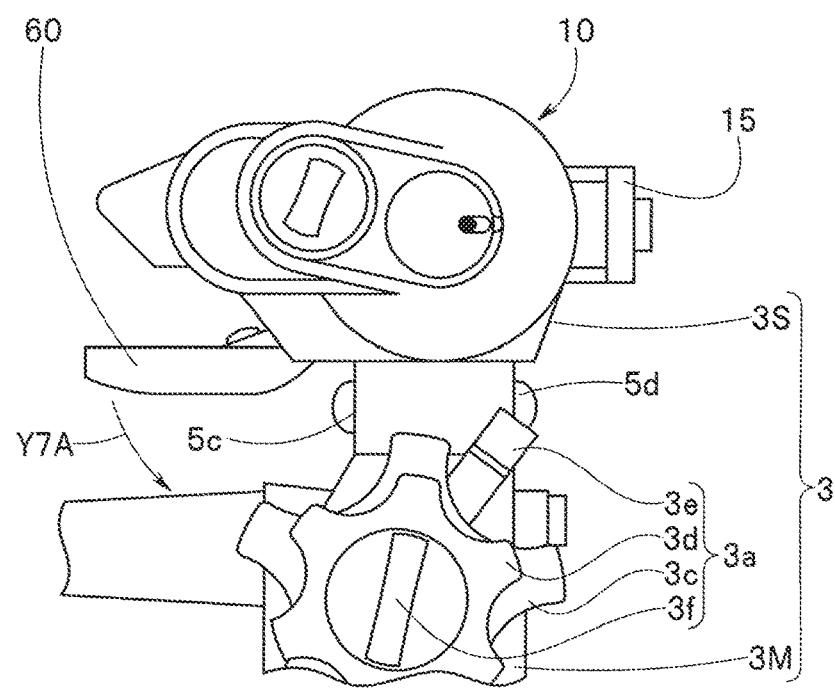
FIG. 7A is a view describing a mounting completion state of the housing case on the sub operation section and an initial position of the operation switch in the completion state.

In such a configuration, as shown in previously mentioned FIG. 2C and FIG. 2D, a user allows the locking pawl portion 15 of the hinge portion 14 to engage with and to be fixed to the locking portion 13. As a result, mounting of the housing case 11 on the sub operation section 3S is completed as shown in FIG. 7A.

In this manner, the concave portion 25 for lever, in which the second bending upward and downward fixing lever 3h can be fitted only when the second bending upward and downward fixing lever 3h, is disposed at the release position is formed in the rotating mechanism portion body 21.

With such a configuration, in a state where the external mechanism for endoscope 10 is attached on the sub operation section 3S, the second bending upward and downward knob 3g can be rotated in a clockwise direction or in a counterclockwise direction with certainty together with the rotation of the knob connecting portion 42.

In other words, in the case where the second bending upward and downward fixing lever 3h is positioned at the position other than the release position, the external mechanism for endoscope 10 prevents the fixing lever 3h from being fitted in the concave portion 25 for lever so as to restrict mounting the housing case 11 on the sub operation section 3S.

Accordingly, it is possible to prevent the occurrence of a defect that a failure occurs in the motor 32 caused by rotating the second bending upward and downward knob 3g the rotary position of which is held, by a drive force of the motor 32.

In other words, the rotating mechanism portion body 21 which is the mounting member also functions as a mounting restricting member.

Figure 7B:
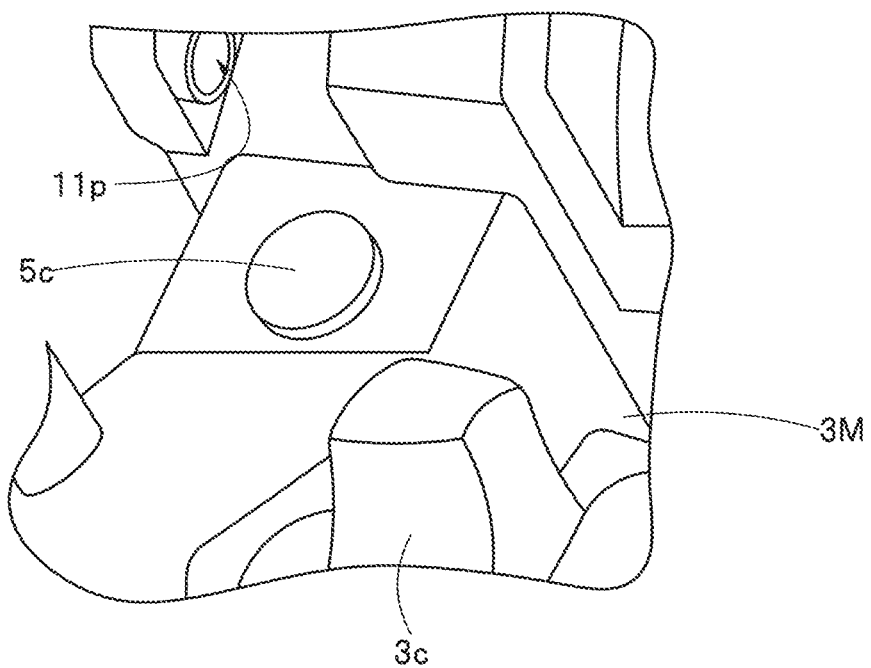
FIG. 7B is a view describing that a remote switch is exposed in the mounting completion state.

As shown in FIG. 7A and FIG. 7B, in a state where the housing case 11 is mounted on the sub operation section 3S, the operation switch 60 is disposed at the initial position and hence, the remote switch 5C is exposed.

After the housing case 11 is mounted on the sub operation section 3S, as shown in FIG. 7A, a user pushes down the switch case 61 of the operation switch 60 which is rotatably mounted on the housing case 11 in a direction indicated by an allow Y7A.

Figure 7C:
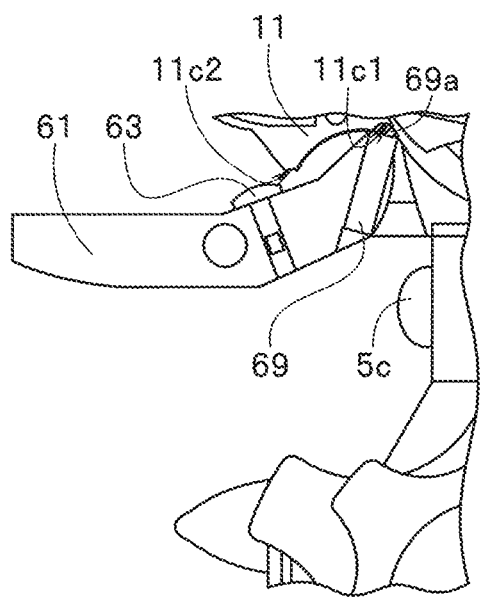
FIG. 7C is a view describing a first engaging state where a slide convex portion of a ball spring plunger is disposed in a first concave portion of the housing case.

As a result, as shown in FIG. 7C, a first engaging state between a slide convex portion 69a of a ball spring plunger 69 provided on the switch case 61 and a first concave portion 11c1 formed on the housing case 11 is released, and the switch case 61 moves toward a space formed between one surface of the main operation section 3M and one end surface of the first betiding upward and downward knob 3c shown in FIG. 7B.

Figure 7D:
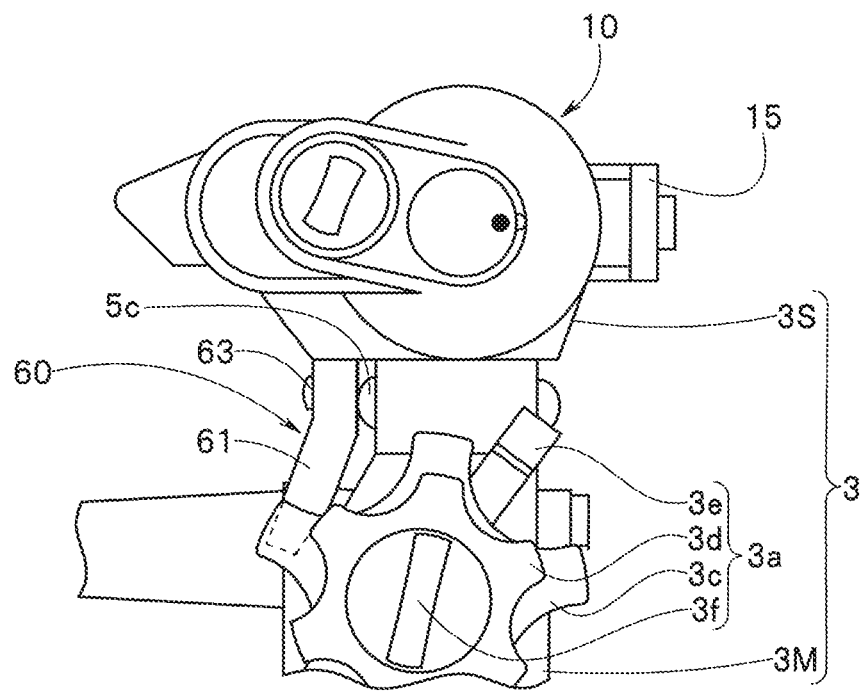
FIG. 7D is a view describing a mechanism attaching state where the operation switch of the external mechanism for endoscope is placed adjacently to a first bending operation device provided to a main operation section.

Then, a second engaging state is brought about due to the engagement between the slide convex portion 69a of the ball spring plunger 69 and a second concave portion 11c2 of the housing case 11 and hence, the movement of the operation switch 60 is completed as shown in FIG. 7D. As a result, the operation switch 60 of the external mechanism for endoscope 10 is placed adjacently to the first bending operation device 3a provided on the main operation section 3M.

As a result, the remote switch 5c which is in an exposed state is brought into a state where the remote switch 5c is covered by the switch case 61.

At this time, a remote switch side of the dummy switch 63 is disposed on the remote switch 5c. In such a state, the remote switch 5c is brought into a switch operable state by operating the dummy switch 63 by pushing.

The manner of operation of the endoscope 1 where the external mechanism for endoscope 10 is mounted on the sub operation section 3S and the operation switch 60 is placed adjacently to the first bending operation device 3a is described.

In performing an endoscope inspection by the endoscope 1 where the external mechanism for endoscope 10 is mounted on the sub operation section 3S, a user grasps the main operation section 3M. Then, the user grasps the insertion section 2 by a hand different from a hand which grasps the main operation section 3M, and inserts the insertion section 2 into a body through an oral cavity, for example.

At this time, the user suitably performs a bending operation of the first bending portion 2b1 and the second bending portion 2b2. In other words, the user bendably operates the first bending portion 2b1 in the upward and downward direction or in the leftward and rightward direction by suitably rotatably operating the first bending upward and downward knob 3c or the first bending leftward and rightward knob 3d of the first bending operation device 3a provided on the main operation section 3M, and the user bendably operates the second bending portion 2b2 in the upward and downward direction by suitably operating the operation element 62 of the operation switch 60 provided adjacently to the first bending operation device 3a of the main operation section 3M.

In this manner, the switch case 61 of the operation switch 60 is rotatably provided on the housing case 11 of the external mechanism for endoscope 10. Further, the ball spring plunger 69 is provided on the switch case 61, and the first concave portion 11c1 and the second concave portion 11c2 are provided on a housing case 11 side.

As a result, in the first engaging state where the slide convex portion 69a of the switch case 61 is disposed in the first concave portion 11c1, at the time of mounting the endoscope external mechanism 10 on the sub operation section 3S, the endoscope external mechanism 10 can be smoothly mounted on the sub operation section 3S without being obstructed by the operation switch 60.

After the endoscope external mechanism 10 is mounted on the sub operation section 3S, the engaging state of the ball spring plunger 69 is switched from the first engaging state to the second engaging state.

With such an operation, the operation switch 60 can be provided adjacently to the first bending operation device 3a of the main operation section 3M. Accordingly, the rotating operation of the first bending upward and downward knob 3c and the first bending leftward and rightward knob 3d of the first bending operation device 3a, the slide operation of the operation element 62 of the operation switch 60 and the like can be performed by a finger of a hand of a user who grasps the main operation section 3M.

Further, the user can more smoothly perform the insertion of the insertion section 2 into a deep portion of a body by suitably performing a bending operation of the first bending portion 2b1 and the second bending portion 2b provided to the bending portion 2b by slightly moving the finger of the hand without touching the remote switch.

In the above-mentioned embodiment, the rotation index 17m is provided to the bending state display portion 17 so as to check a bending angle.

Figure 8:
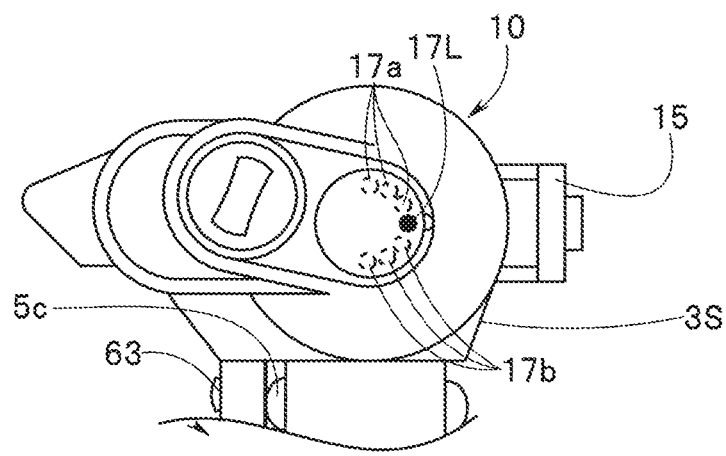
FIG. 8 is a view describing another configurational example of a bending state display part.

However, as shown in FIG. 8, the rotation index may be an LED lamp 17L. The larger a bending amount of the second bending portion 2b2, the smaller a flickering interval of the LED lamp 17L becomes. When the second bending portion 2b2 approaches a maximum bending state, the LED lamp 17L is brought into a lit state. The bending direction of the second bending portion 2b2 is determined based on the operation direction of the operation element 62.

In the above-mentioned embodiment, the rotation index 17m is formed of one LED lamp 17L. However, a plurality of LED lamps 17a, 17b may be arranged around the LED lamp 17L using the LED lamp 17L as a reference lamp. With such a configuration, it is possible to check that a bending amount of the bending portion 2b2 is increased along with the increase of the number of the lit LED lamps.

In the above-mentioned description, the external mechanism for endoscope 10 is attached on the sub operation section 3S so as to allow a user to perform a bending operation of the second bending portion 2b2 while preventing a large load from being applied to fingers of the user.

However, the knob on which the external mechanism for endoscope 10 is attached is not limited to the second bending upward and downward knob 3g formed on the sub operation section 3S. The external mechanism for endoscope 10 may be attached on the first bending leftward and rightward knob 3d provided on the main operation section 3M, or may be attached on both the first bending upward and downward knob 3c and the first bending leftward and rightward knob 3d.

The present invention is not limited to the above-mentioned embodiment, and various modifications of the present invention are conceivable without departing from the gist of the present invention.

What is claimed is:

1. An external mechanism comprising:
    a bending wheel configured to matingly engage with a bending operation knob of a bending operation device provided to an operation section of an endoscope, the endoscope further having a locking knob provided to the operation section of the endoscope and being displaceable between a locking position at which a rotary position of the bending operation knob is locked and a rotating position at which locking of the rotation of the bending operation knob is released;
    a motor configured to generate a drive force for rotating the bending wheel;
    a housing case housing the bending wheel and the motor;
    a clamp for detachably mounting the housing case on the operation section;
    a mounting restricting member having a surface configured to obstruct mounting of the housing case on the operation section by interfering with the locking knob in a state where the locking knob is disposed at a position other than the rotating position;
    a driven gear provided on the bending wheel;
    a drive gear provided on the motor to transmit a rotation of the drive force; and
    a switching gear movable between a first state and a second state;
    wherein in the first state, the switching gear meshes with the driven gear and the drive gear and the switching gear is provided between the driven gear and the drive gear to transmit the rotation of the drive force from the drive gear to the driven gear, and
    in the second state, the switching gear is disconnected from the drive gear and the driven gear.

2. The external mechanism according to claim 1, wherein the locking knob is a lever which is rotatably operated about a rotation axis of the bending operation knob, and
    the surface is positioned at an inner periphery of the bending wheel, and the surface defines a recess, the locking knob being fitted into the recess only in a state where the locking knob is at the rotating position.

3. The external mechanism according to claim 1, wherein the surface comprises a plurality of surfaces forming a concave portion.

4. The external mechanism according to claim 1, further comprising a switch for providing a drive control signal to the motor.

5. The external mechanism according to claim 1, the external mechanism further comprising a switching tab connected to the switching gear, and the switching tab switching the switching gear between the first state and the second state by rotation of the switching tab.

6. An endoscope system comprising:
an endoscope; and
an external mechanism detachably mounted on an operation section of the endoscope, wherein
the endoscope includes:
a bending knob provided to the operation section and configured to bend a bending portion of an insertion section by being rotated; and
a locking knob provided to the operation section, the locking knob being displaceable between a locking position at which a rotation position of an operation knob is locked and a rotating position at which locking of the rotation of the operation knob is released by being operated, and
the external mechanism includes:
a wheel matingly engaging with the bending knob so as to rotate the bending knob;
a motor configured to generate a drive force for rotating the wheel;
a housing case housing the wheel and the motor;
a clamp for detachably mounting the housing case on the operation section; and
a mounting restricting member having a surface configured to obstruct mounting of the housing case on the operation section by interfering with the locking knob in a state where the locking knob is disposed at a position other than the rotating position;
the external mechanism further comprising:
a driven gear provided on the bending wheel;
a drive gear provided on the motor to transmit a rotation of the drive force;
a switching gear movable between a first state and a second state;
wherein in the first state, the switching gear meshes with the driven gear and the drive gear and the switching gear is provided between the driven gear and the drive gear to transmit the rotation of the drive force from the drive gear to the driven gear, and
in the second state, the switching gear is disconnected from the drive gear and the driven gear.

7. The endoscope system according to claim 6, wherein the locking knob is a lever which is rotatably operated coaxially with a rotation axis of the operation knob, and
the surface is positioned at an inner periphery of the wheel, and the surface defines a recess, the locking knob being fitted into the recess only in a state where the knob operation holding portion is at the release position.

8. The endoscope system according to claim 6, wherein the surface comprises a plurality of surfaces forming a concave portion.

9. The endoscope system according to claim 6, wherein the external mechanism further comprising a switch for providing a drive control signal to the motor.

10. The endoscope system according to claim 9, wherein the bending knob comprising a first bending knob, the bending section comprising a first bending section and the operation section comprising a first operation section, the endoscope further comprising:

a second operation section provided proximally relative to the first operation section;
a second bending knob provided to the second operation section and configured to bend a second bending portion of the insertion section by being rotated; and
wherein the switch is arranged next to the second bending knob.

11. The endoscope system according to claim 10, the endoscope further comprising a universal cord extended from the second operation section; and
wherein the switch is arranged between the second bending knob and the universal cord.

12. The endoscope system according to claim 6, the external mechanism further comprising a switching tab connected to the switching gear, and the switching tab switching the switching gear between the first state and the second state by rotation of the switching tab.

13. The endoscope system according to claim 6, the external mechanism further comprising a bending state display configured to display a rotation of the bending wheel, the bending state display having a rotation index, and
the bending state display changes the rotation index according to the rotation of the bending wheel.

14. The endoscope system according to claim 13, wherein the rotation index is a mark in a predetermined position, a position of the rotation index is changed by a rotation of the bending state display.

15. The endoscope system according to claim 13, wherein the rotation index is an LED lamp, and a flickering interval of the LED lamp is changed by the rotation of the bending wheel.

16. An external mechanism comprising:
a bending wheel configured to matingly engage with a bending operation knob of a bending operation device provided to an operation section of an endoscope, the endoscope further having a locking knob provided to the operation section of the endoscope and being displaceable between a locking position at which a rotary position of the bending operation knob is locked and a rotating position at which locking of the rotation of the bending operation knob is released;
a motor configured to generate a drive force for rotating the bending wheel;
a housing case housing the bending wheel and the motor;
a clamp for detachably mounting the housing case on the operation section;
a mounting restricting member having a surface configured to obstruct mounting of the housing case on the operation section by interfering with the locking knob in a state where the locking knob is disposed at a position other than the rotating position; and
a bending state display configured to display a rotation of the bending wheel, the bending state display having a rotation index, and the bending state display changes the rotation index according to the rotation of the bending wheel.

17. The external mechanism according to claim 16, wherein the rotation index is a mark in a predetermined position, a position of the rotation index is changed by a rotation of the bending state display.

18. The external mechanism according to claim 16, wherein the rotation index is an LED lamp, and a flickering interval of the LED lamp is changed by the rotation of the bending wheel.

* * * * *